United States Patent [19]
Barth et al.

[11] Patent Number: 5,942,630
[45] Date of Patent: Aug. 24, 1999

[54] PROCESS FOR THE PRODUCTION OF ENANTIOMERICALLY-PURE AZETIDINE-2-CARBOXYLIC ACID

[75] Inventors: Philipp Barth, Zürich; Hugo Fritschi, Uznach; Jan-Erik Nyström, Lindome; Armin Pfenninger, Uetikon, all of Switzerland

[73] Assignee: Astra AB, Sodertalje, Sweden

[21] Appl. No.: 08/716,388

[22] PCT Filed: Jun. 24, 1996

[86] PCT No.: PCT/SE96/00826

§ 371 Date: Sep. 19, 1996

§ 102(e) Date: Sep. 19, 1996

[87] PCT Pub. No.: WO97/02241

PCT Pub. Date: Jan. 23, 1997

[30] Foreign Application Priority Data

Jun. 30, 1995 [SE] Sweden ................................ 9502381
Feb. 6, 1996 [SE] Sweden ................................ 9600435

[51] Int. Cl.$^6$ .................................................. C07D 205/04
[52] U.S. Cl. ................................................................. 548/953
[58] Field of Search ............................................. 548/953

[56] References Cited

PUBLICATIONS

Fowden, L., "Azetidine–2–carboxylic Acid: A new Cyclic Imino Acid Occurring in Plants," Biochem. J., vol. 64, pp. 323–332 (1956).

Rodebaugh et al., "A Facile New Synthesis of DL–Azetidine–2–Carboxylic Acid (1a)," J. Heterocyclic Chem., vol. 6, pp. 435–437 (1969).

Rodebaugh et al., "Resolution of DL–Azetidine–2–carboxylic Acid," J. Heterocyclic Chem., vol. 6, pp. 993–994, Dec. 1996.

Cromwell et al., "The Azetidines, Recent Synthetic Developments," Chemical Reviews, vol. 79, No. 4, pp. 331–354 ((1979).

Yokoyama et al., "The Decomposition Product of Ethyl 2–Cyano–3–mercapto–3–methylthioacrylate," Bull. Chem. Soc. Japan, vol. 46, pp. 669–700 (1973).

Shiraiwa et al, "Asymmetric Transformations of Proline and 2–Piperidinecarboxylic . . . ," Bull. Chem. Soc. Jpn., vol. 64, pp. 3251–3255 (1991).

Primary Examiner—Deborah C. Lambkin
Assistant Examiner—Ebenezer Sackey
Attorney, Agent, or Firm—Nixon & Vanderhye

[57] ABSTRACT

The invention relates to a process for the production of enantiomerically-pure AzeOH which comprises selective crystallisation of a diastereomerically-pure tartrate salt thereof, followed by liberation of the free amino acid, as well as the compounds L-azetidine-2-carboxylic acid-D-tartrate and D-azetidine-2-carboxylic acid-L-tartrate.

15 Claims, No Drawings

PROCESS FOR THE PRODUCTION OF ENANTIOMERICALLY-PURE AZETIDINE-2-CARBOXYLIC ACID

This application is a 371 of PCT/SE96/00826 filed on Jun. 24, 1996.

FIELD OF THE INVENTION

This invention relates to a process for the production of enantiomerically pure azetidine-2-carboxylic acid.

PRIOR ART

L-Azetidine-2-carboxylic acid (L-AzeOH) is a known to be useful in the synthesis of inter alia high molecular weight polypeptides and in particular as an analogue of the well known amino acid proline.

Previously documented preparations of enantiomerically-pure AzeOH (ie D- and/or L-AzeOH) from the racemate (DL-AzeOH) involve long and relatively complicated multi-step methodology.

A four step preparation involving the protection, resolution and subsequent deprotection of DL-AzeOH is known from J. Heterocylic Chem. (1969) 6, 993. In this method, N-carbobenzoxy-protected DL-AzeOH is resolved using L-tyrosine hydrazide as resolution agent, and then isolated before a final deprotection step. This process has the further disadvantage that L-tyrosine hydrazide is expensive.

Other reported preparations of L-AzeOH include a five step preparation via homoserine lactone, starting from N-tosyl protected L-methionine (see eg Japanese Patent Application N°14457/74 and Bull. Chem. Soc. Jpn. (1973) 46, 669 and a five step preparation via L-4-amino-2-chlorobutyric acid, starting from L-2,4-diaminobutyric acid (see Biochem. J. (1956) 64, 323).

DESCRIPTION OF THE INVENTION

Tartaric acid has been known for many years to exist in three stereochemical forms, the L-form, the D-form and the meso-form. Two of these diastereoisomers, L- and D-tartaric acid are enantiomers.

We have now surprisingly found that enantiomerically-pure AzeOH may be produced in extremely high yields via a novel and efficient process which comprises the formation of a homogeneous solution of racemic AzeOH and of either D- or L-tartaric acid, crystallisation of the resultant tartrate salt from solution, and subsequent liberation of the free amino acid.

In particular, we have found that crystallisation of racemic AzeOH with D-tartaric acid produces extremely high yields diastereomerically-pure of L-AzeOH-D-tartrate in the crystalline form, from which optically-pure L-AzeOH may be liberated. Similarly we have found that crystallisation using L-tartaric acid produces extremely high yields of diastereomerically-pure D-AzeOH-L-tartrate, from which optically-pure D-AzeOH may be liberated.

According to the invention there is provided a process for the production of enantiomerically-pure AzeOH which comprises selective crystallisation of a diastereomerically-pure tartrate salt thereof, followed by liberation of the free amino acid.

By "selective crystallisation" we mean crystallisation of a diastereomerically-pure AzeOH-tartrate salt from a homogeneous solution of racemic AzeOH and one or other of D- or L-tartaric acid.

Although the process according to the invention may be used to produce either L-AzeOH-D-tartrate or D-AzeOH-L-tartrate with a diasteromeric excess (d.e.) greater than 90%, by "diastereomerically-pure AzeOH-tartrate salt" we mean a AzeOH-tartrate salt with a d.e. of greater than 40%.

Although the process according to the invention may be used to produce either L-AzeOH or D-AzeOH with optical purities (enantiomeric excess; e.e.) of greater than 90%, by "enantiomerically-pure AzeOH" we mean an AzeOH enantiomer with an e.e. of greater than 50%.

Suitable solvent systems in which racemic AzeOH and tartaric acid may be dissolved include one or more organic solvents, with or without the presence of water. Organic solvents which may be employed include those which are miscible with and/or soluble in water and in which the diastereomerically-pure AzeOH-tartrate salts are poorly soluble at room temperature or below. Examples of suitable organic solvents include monofunctional alcohols (eg ethanol, methanol or isopropanol), difunctional alcohols (eg ethylene glycol), $C_{1-8}$ mono- or divalent carboxylic acids (eg formic or acetic acid), $C_{4-6}$ linear or cyclic ethers (eg monoglyme, diglyme, tetrahydrofuran or dioxane). Particularly preferred organic solvents include ethanol and $C_{1-3}$ carboxylic acids.

Following dissolution of racemic AzeOH and L- or D-tartaric acid in the solvent system, the mixture may, if necessary, be adjusted to form a homogeneous solution by appropriate means, for example by heating to elevated temperature (eg at reflux).

Suitable molar ratios of L- or D-tartaric acid to racemic AzeOH which may be employed are in the range 0.5:1.0 to 2.0:1.0, preferably 0.6:1.0 to 1.1:1.0 and particularly 0.8:1.0 to 1.0:1.0.

Crystallisation of the diastereomerically-pure AzeOH-tartrate salt is achieved by cooling the solution of AzeOH and tartaric acid to supersaturation temperature. Final crystallisation temperatures for the above mentioned solvent systems are typically in the range −10 to 30° C., for example −5 to 10° C. and preferably 0 to 5° C.

Crystallisation may be effected with or without seeding with crystals of the appropriate diastereomerically-pure AzeOH-tartrate salt. However, we prefer crystallisation to be effected by seeding.

The crystalline salt may be isolated using techniques which are well known to those skilled in the art, for example decanting, filtering or centrifuging.

Liberation of the enantiomerically-pure free amino acid from the crystalline salt following selective crystallisation may be achieved by displacing tartaric acid from the AzeOH-tartrate salt by reacting with a carbonate, an oxide, a hydroxide or a chloride of a metal which is known to form salts with tartaric acid (eg calcium or potassium). Particularly preferred calcium salts include calcium chloride. Particularly preferred potassium salts include potassium hydroxide. The displacement reaction may be performed above room temperature (eg between 30 and 60° C.) in the presence of an appropriate solvent in which AzeOH is soluble and the metal-tartrate salt is poorly soluble (eg water). Free optically pure amino acid may be separated from the precipitated metal tartrate (or hydrogen tartrate) by conventional techniques (eg filtering, centrifuging or decanting).

Enantiomerically-pure D- or L-AzeOH may be further purified using conventional techniques (eg recrystallisation from an appropriate solvent, such as acetone or water, or combinations thereof).

The process according to the invention may also be used to optically enrich optically impure AzeOH-tartrate salts.

Racemic AzeOH may be prepared according to methods described in the literature (see eg J. Heterocyclic Chem. (1969) 6, 435 and ibid (1973) 10, 795).

The process according to the invention has the advantage that enantiomerically pure AzeOH may be prepared in higher yields, with greater optical purity, in a manner which involves fewer steps (and without the need for protecting groups), in less time, more conveniently and at a lower cost than processes previously employed for the production of enantiomerically pure AzeOH. Moreover, tartaric acid may be recovered from the process according to the invention in a form which is pure enough for further use in the process (ie tartaric acid may be recycled without the need for additional purification). The invention is illustrated, but in no way limited, by the following examples. The crystalline products were analysed for AzeOH content by dissolving a sample in acetic acid:formic acid (40:3) followed by titration with 0.1 M perchloric acid, and for tartaric acid content by titration with 0.1 M sodium hydroxide. Optical purity was determined using HPLC (UV, 250 nm) on GITC-derivitised samples (see J. Chromat. (1980) 202, 375) using a silica column (Kromasil C8, 5$\mu$m, 150×4.6 mm) eluting with 35% methanol and 65% water containing 0.1% trifluoroacetic acid.

EXAMPLES

Preparation of L-Azetidine-2-carboxylic acid-D-tartrate (L-AzeOH-D-tartrate)

EXAMPLE 1

DL-AzeOH (7.08 g; 70 mmol) and D-tartaric acid (10.5 g; 70 mmol) were suspended in ethanol (94%; 30 g) and water (25 g). Heating the resultant solution to reflux produced a homogeneous solution. After heating, a crystal of L-AzeOH-D-tartrate was added, and the whole cooled gradually to 0° C. This temperature was maintained for 2 hours. The crystalline product was filtered, washed with the solvent system and dried under vacuum at 50° C. to yield 8.1 g (92%) of L-AzeOH-D-tartrate with a d.e. of 95%.

EXAMPLE 2

The method described in Example 1 above was followed using DL-AzeOH (2.0 g; 20 mmol), D-tartaric acid (5.5 g; 36.6 mol), ethanol (94%; 6.7 g) and water (3.3 g) to yield 2.5 g (100%) of L-AzeOH-D-tartate with a d.e. of 85%.

EXAMPLE 3

The method described in Example 1 above was followed using DL-AzeOH (3.7 g; 37 mmol), D-tartaric acid (3.0 g; 20.0 mmol), ethanol (4.5 g) and water (5.5 g) to yield 3.8 g (83%) of L- AzeOH-D-tartrate with a d.e. of 95%.

EXAMPLE 4

The method described in Example 1 above was followed using DL-AzeOH (2.9 g; 29 mmol), D-tartaric acid (4.3 g; 29 mmol), ethylene glycol (5.5 g) and water (4.5 g) to yield 3.9 g (109%, as calculated from the theoretical yield) of L-AzeOH-D-tartrate with a d.e. of 60%.

EXAMPLE 5

The method described in Example 1 above was followed using DL-AzeOH (2.9 g; 29 mmol), D-tartaric acid (4.3 g; 29 mmol), tetrahydrofuran (5.5 g) and water (4.5 g) to yield 3.9 g (109%, as calculated from the theoretical yield) of L-AzeOH-D-tartrate with a d.e. of 65%.

EXAMPLE 6

The method described in Example 1 above was followed using DL-AzeOH (2.9 g; 29 mmol), D-tartaric acid (4.3 g; 29 mmol), 1,4-dioxane (5.5 g) and water (4.5 g) to yield 3.4 g (109%, as calculated from the theoretical yield) of L-AzeOH-D-tartrate with a d.e. of 73%.

EXAMPLE 7

L-AzeOH-D-tartrate (4.0 g; e.e. of 10%) was suspended in ethanol (10.7 g) and water (9.3 g). Heating the resultant solution to reflux produced a homogeneous solution. After heating, a crystal of L-AzeOH-D-tartrate was added and the whole cooled gradually to 0° C. This temperature was maintained for 2 hours. The crystalline product was filtered, washed with the solvent system and dried under vacuum at 50° C. to yield 2.0 g of L-AzeOH-D-tartrate with a d.e. of 96%.

EXAMPLE 8

The method described in Example 1 may be followed using acetic acid instead of ethanol.

Preparation of L-Azetidine-2-carboxylic acid (L-AzeOH)

EXAMPLE 9

L-AzeOH-D-tartrate (7.2 g; 28 mmol; e.e. of 99%) was dissolved in hot water (16 mL). At about 45° C. aqueous potassium hydroxide (6 mL; 6 M; 24 mmol) was added over 15 minutes. The solution was cooled to 5° C. at which temperature potassium hydrogen tartrate was formed, which was filtered and washed with cold water (3 mL). The combined filtrate was concentrated under vacuum to give a crude product which was stirred for 1 hour at 60° C. with water (1 mL) and acetone (30 mL). The product was filtered off and dried to yield 2.5 g (89%) of L-AzeOH with an e.e. of 96%.

Preparation of D-Azetidine-2-carboxylic acid-L-tartrate (D-AzeOH-L-tartrate)

EXAMPLE 10

The method described in Example 1 above may be followed using DL-AzeOH, L-tartaric acid, ethanol and water to yield D-AzeOH-L-tartrate.

Preparation of D-Azetidine-2-carboxylic acid (D-AzeOH)

EXAMPLE 11

The method described in Example 9 above may be followed using D-AzeOH-L-tartrate, water and potassium hydroxide to yield D-AzeOH.

We claim:

1. A process for the production of enantiomerically-pure AzeOH which comprises selective crystallisation of a diastereomerically-pure tartrate salt thereof, followed by liberation of the free amino acid.

2. A process according to claim 1, wherein the selective crystallisation is from a solvent system which comprises water and one or more organic solvent.

3. A process according to claim 2, wherein the organic solvent is selected from the group consisting of one or more alcohols, $C_{1-8}$ carboxylic acids, $C_{4-6}$ linear ethers and $C_{4-6}$ cyclic ethers.

4. A process according to claim 2, wherein the organic solvent is ethanol.

5. A process according to claim 1, wherein the organic solvent is a $C_{1-3}$ carboxylic acid.

6. A process according to claim 1, wherein the selective crystallisation is from a solution which comprises a molar ratio of enantiomerically pure tartaric acid to racemic azetidine-2-carboxylic acid in the range 0.5:1.0 to 2.0:1.0.

7. A process according to claim 6 wherein the molar ratio is in the range 0.6:1.0 to 1.1:1.0.

8. A process according to claim 6, wherein the molar ratio is in the range 0.8:1.0 to 1.0 to 1.0.

9. A process according to claim 1, wherein the selective crystallisation is achieved by cooling to a temperature in the range −10 to 30° C.

10. A process according to claim 9, wherein the temperature is in the range −5 to 10° C.

11. A process according to claim 10, wherein the temperature is in the range 0 to 5° C.

12. A process according to claim 1, wherein the free amino acid is liberated by displacement of tartaric acid using calcium chloride.

13. A process according to claim 1, wherein the free amino acid is liberated by displacement of tartaric acid using potassium hydroxide.

14. L-Azetidine-2-carboxylic acid D-tartrate.

15. D-Azetidine-2-carboxylic acid L-tartrate.

* * * * *